United States Patent
Lee et al.

(10) Patent No.: US 9,062,262 B2
(45) Date of Patent: Jun. 23, 2015

(54) PROCESS FOR 1,3-BUTADIENE SEPARATION FROM A CRUDE C4 STREAM WITH ACETYLENE CONVERTER

(75) Inventors: Hee Du Lee, Daejeon (KR); Kyung Jong Oh, Daejeon (KR); Min Su Ko, Daejeon (KR); Min Gyoo Park, Ulsan (KR); Seong Jun Lee, Daejeon (KR); Yoon Jae Yim, Chungcheongnam-do (KR); Seung Hoon Oh, Seoul (KR); Tae Jin Kim, Daejeon (KR); Yong Seung Kim, Seoul (KR); Deuk Soo Park, Goyang-si (KR); Hong Chan Kim, Jeju-do (KR)

(73) Assignee: SK INNOVATION CO., LTD., Seoul (KR)

( * ) Notice: Subject to any disclaimer, the term of this patent is extended or adjusted under 35 U.S.C. 154(b) by 1089 days.

(21) Appl. No.: 12/452,715

(22) PCT Filed: Jul. 18, 2008

(86) PCT No.: PCT/KR2008/004220
§ 371 (c)(1),
(2), (4) Date: Jan. 14, 2010

(87) PCT Pub. No.: WO2010/008109
PCT Pub. Date: Jan. 21, 2010

(65) Prior Publication Data
US 2010/0137664 A1    Jun. 3, 2010

(30) Foreign Application Priority Data
Jul. 17, 2008 (KR) .................. 10-2008-0069677

(51) Int. Cl.
*C10G 67/04* (2006.01)
*C07C 7/08* (2006.01)
(Continued)

(52) U.S. Cl.
CPC . *C10G 67/04* (2013.01); *C07C 7/08* (2013.01); *C07C 11/107* (2013.01); *C10G 21/00* (2013.01);
(Continued)

(58) Field of Classification Search
CPC ........ C10G 67/02; C10G 67/04; C10G 21/00; C10G 21/28; C10G 45/32; C10G 23/44; C10G 2400/20; C07C 7/08; C07C 11/107

USPC ......... 585/258, 259, 265, 610, 810, 802, 264, 585/601, 809
See application file for complete search history.

(56) References Cited

U.S. PATENT DOCUMENTS 3,567,794 A * 3/1971 Eberly et al. .................. 585/326
3,772,158 A * 11/1973 Sarno ............................. 203/53

(Continued)

FOREIGN PATENT DOCUMENTS

| EP | 0931042 B1 * | 7/2002 | ............. C07C 7/163 |
| JP | 53040702 | 4/1978 | |
| JP | 57123123 | 7/1982 | |

OTHER PUBLICATIONS

Paul N. Rylander, "Hydrogenation and Dehydrogenation," 2005, Wiley-VCH, Ullman's Encyclopedia of Industrial Chemistry, p. 3.*

(Continued)

*Primary Examiner* — In Suk Bullock
*Assistant Examiner* — Philip Louie
(74) *Attorney, Agent, or Firm* — Abelman, Frayne & Schwab

(57) ABSTRACT

Disclosed is a method of recovering 1,3-butadiene from a C4 stream containing butane, isobutane, 2-butene, 1-butene, isobutene, butadiene and acetylene. The process of recovering highly pure 1,3-butadiene includes acetylene conversion for selectively converting acetylene through liquid-phase hydrogenation, so that the acetylene content is decreased to 70 wt ppm or less, and 1,3-butadiene extraction using an extractive distillation column, a pre-separator, a solvent stripping column, a solvent recovery column, and a purification column. Through the acetylene conversion, the concentration of vinylacetylene is decreased to 70 wt ppm or less, after which 1,3-butadiene is recovered using only one extractive distillation column, thereby considerably decreasing the degree of utility and the loss of streams in the course of extraction. The number of units necessary for the process is decreased, thus remarkably reducing the time during which impurities can accumulate in a processing unit.

13 Claims, 5 Drawing Sheets

(51) Int. Cl.
  *C10G 21/00*  (2006.01)
  *C07C 11/107*  (2006.01)
  *C10G 21/28*  (2006.01)
  *C10G 45/32*  (2006.01)

(52) U.S. Cl.
  CPC ............. *C10G 21/28* (2013.01); *C10G 45/32* (2013.01); *C10G 2300/44* (2013.01); *C10G 2400/20* (2013.01)

(56) References Cited

U.S. PATENT DOCUMENTS

| | | | |
|---|---|---|---|
| 4,038,156 A | | 7/1977 | Knott et al. |
| 4,128,457 A | | 12/1978 | Barba et al. |
| 4,277,313 A | * | 7/1981 | Mehra et al. .................. 203/32 |
| 4,704,492 A | * | 11/1987 | Nemet-Mavrodin ......... 585/259 |
| 4,859,286 A | | 8/1989 | Kaibel et al. |
| 5,264,117 A | * | 11/1993 | DeLong ........................ 208/354 |
| 6,011,188 A | * | 1/2000 | Crewdson et al. ............ 585/259 |
| 6,015,933 A | * | 1/2000 | Abrevaya et al. ............. 585/810 |
| 6,040,489 A | | 3/2000 | Imai |
| 6,040,689 A | | 3/2000 | Gluszek |
| 7,226,527 B2 | | 6/2007 | Bohner et al. |

OTHER PUBLICATIONS

Extended Search Report dated Nov. 29, 2011 issued by the EPO regarding Application No. 08778875.8-2104/2310474.
Jalali et al.; "Simulation and Optimization in 1,3-Butadiene Process for C4-Cut Using Genetic Algorithm"; 16th European Symposium on Computer Aided Process Engineering and 9th International Symposium on Process Systems Engineering; Dec. 31, 2006, Elsevier B.V., XP002662587; pp. 901-906.
Burrows; "Butadiene Product Stewardship Guidance Manual Rev Mar. 10, 2002", American Chemistry Council; Oct. 3, 2002; XP002662585.
Lei Zhigang et al.; "Process Design for Separating C4 Mixtures by Extractive Distillation"; Chinese J. Chem. Eng.; Dec. 31, 2003; pp. 297-301; vol. 11, No. 3; XP002662586.
Office Action from the Japanese Patent Office for Japanese Patent Application No. 2011-518606 dated Feb. 13, 2013. (Summary of Office Action in English enclosed).
Beth McCulloch, Charles Luebke, and Jill Meister, "Selective Hydrogenation Processes", The Handbook of Petroleum Refining Processes (McGraw-Hill, 3rd Ed.), 2004, pp. 8.25-8.29.
Office Action from the Chinese Patent Office dated Apr. 8, 2013 for Application No. 2008801046109. (Summary of Office Action in English enclosed).

* cited by examiner

PROCESS FOR 1,3-BUTADIENE SEPARATION FROM A CRUDE C4 STREAM WITH ACETYLENE CONVERTER

TECHNICAL FIELD

The present invention relates to a method of recovering highly pure 1,3-butadiene through selective hydrogenation to remove acetylenes from a crude C4 stream consisted of butane, isobutane, 2-butenes, 1-butene, isobutene, butadienes and acetylenes.

BACKGROUND ART

Generally, method of separating highly pure 1,3-butadiene from crude C4 stream, which is discharged from a cracker and contains acetylenes, uses the butadiene extraction unit (BEU) with two extractive distillation columns (EDC).

It is inevitable to lose the 1,3-Butadiene because it is used as a diluent to eliminate potential explosion of the vinylacetylene in conventional butadiene extraction unit.

In present extraction units, the bottom temperature of a 1,3-butadiene recovery column, which is used for recovering some 1,3-butadienes from the bottom stream of the $2^{nd}$ EDC, is dependent on vinylacetylenes to 1,3-butadiene ratio of C4 feed stream of the $1^{st}$ EDC. 1,3-Butadiene recovery can be improved by increasing operating temperature of 1,3-butadiene recovery column when their ratio is low. However, in case of the C4 stream with more than 1.2 wt % of vinylacetylene, the bottom stream of 1,3-butadiene recovery column should be diluted by means of adding 1,3-butadiene to avoid the explosion threshold of vinylacetylene. Thus, it is difficult to increase the temperature of 1,3-butadiene recovery column more than 130° C. So 1,3-butadiene recovery in overall process is only 96~97%. Additionally, acetylene contamination of columns and heat-exchangers restricts long term operation of BEU.

To solve these problems, a method to remove acetylenes (particularly vinylacetylene) beforehand in BEU feedstocks has been proposed.

The crude C4 mixtures from a naphtha cracker is consisted of 0.5~2.0 wt % of vinylacetylene, 0.1~0.3 wt % ethylacetylene, and 0.01~0.10 wt % methylacetylene. There are two methods of removing acetylenes through hydrogenation to convert acetylenes into 1,3-butadiene, 1-butene and propylenes, respectively, and BEU with two-EDCs.

The Handbook of Petroleum Refining Process (McGraw-Hill, $3^{rd}$ ed., Chapter 8.2(8.25), 2004) discloses the process of producing highly pure 1,3-butadiene by integrating a KLP™ process with two or three hydrogenation reactors and BEU with only one EDC. The KLP™ process includes not only removing unit for sulfur compounds to prevent the deactivation of a Cu-based catalyst in the C4 mixtures but also a water washing unit. In this process, the recycled C4 mixtures are fed to the reactor along with fresh C4 mixtures and hydrogen. The hydrogenation is performed at 15 kg/cm$^2$·g and 30~50° C. by using two reactors. Recently, to increase the solubility of hydrogen, the reactor has been designed to be affordable for operation at 40 kg/cm$^2$·g and 60~70° C. Then the hydrogenation product is fed to the distillation column, so that the C4 stream is obtained from the bottom and a light gas component is discharged from the column overhead. However, this process has defect of requiring increased energy consumption because of using additional refrigerator to prevent loss of the C4 mixtures when the light gases are removed at column overhead.

There are some other conventional techniques which integrate selective hydrogenation of acetylenes in the C4 mixtures other than the KLP™ process and BEU for 1,3-butadiene purification. U.S. Pat. No. 4,277,313 includes a hydrogenation to remove acetylenes and BEU in which the overhead stream of the $2^{nd}$ solvent recovery column is recycled into the hydrogenation reactor along with the C4 mixtures.

However, in this case, overhead stream of the $2^{nd}$ solvent recovery column includes 1,3-butadiene in almost as the same amount to that of vinylacetylene along with a large amount of solvent. However, the recycle of overhead stream of the $2^{nd}$ solvent recovery column is problematic in that the gas phase of it must be additionally condensed to increase the pressure before introducing it into the hydrogenation reactor because only gas phase of it is recycled.

The hydrogen used for hydrogenation should be completely dissolved in the C4 mixtures and the molar ratio of hydrogen to acetylene should be more than 1. However, hydrogen cannot be dissolved to the required ratio because hydrogenation in above patent is performed at 6 kg/cm$^2$·g and 30° C. It is impossible to completely convert acetylenes in this condition. U.S. Pat. No. 6,040,689 suggests reactive extractive distillation column which integrates a hydrogenation with a Cu-based catalyst into an extractive distillation.

In order to connect the selective hydrogenation of acetylenes in crude C4 mixtures with dienes and the extraction process, the reaction stability of the acetylene converter, a long-term to operation and easiness of catalyst regeneration are required basically. Furthermore, in order to simplify the process and increase economical efficiency, only one EDC operation is preferable. To recover highly pure 1,3-butadiene by using only one EDC after the selective hydrogenation process, the loss of 1,3-butadiene and vinylacetylene concentration of hydrogenation effluent should be less than 1 wt % and less than 70 ppm respectively.

DISCLOSURE

Technical Problem

The present invention provides a method and equipments to separate highly pure 1,3-butadiene from a crude C4 stream containing butane, isobutane, 2-butenes, 1-butene, isobutene, butadienes and acetylenes.

Technical Solution

According to this invention, a method of separating highly pure 1,3-butadiene from rude C4 mixtures comprises (a) supplying the crude C4 mixtures into hydrogenation reactors; (b) selectively converting acetylenes in the C4 mixtures through liquid-phase hydrogenation by using hydrogenation reactors to decrease a content of acetylenes less than 70 wt ppm; (c) supplying stream after the hydrogenation reactors into an EDC along with extraction solvent and then conducting extractive distillation; (d) supplying a bottom stream of the EDC into a pre-separator, feeding an top gas-phase stream of the pre-separator into the solvent recovery column and feeding a bottom liquid-phase stream of the pre-separator into the solvent stripping column; (e) supplying an overhead stream of the solvent stripping column containing part of extraction solvent, butadienes and acetylenes into the solvent recovery column along with the top gas-phase stream of the pre-separator; and (f) supplying a overhead stream of the solvent recovery column, in which the extraction solvent is removed, into purification columns to obtain highly pure 1,3-butadiene.

In addition, according to the present invention, equipments for separating 1,3-butadiene comprise hydrogenation reactors for selectively converting acetylenes in a crude C4 stream through liquid-phase hydrogenation; an Extractive distillation column (EDC) to extract 1,3-butadiene in a stream from hydrogenation reactors; separator to remove unreacted hydrogen from the hydrogenation; heavies stripping column to remove hydrocarbons with more than 5 carbons and green oil; a pre-separator to adjust the content of extraction solvent in the top gas-phase stream toward solvent recovery column; a solvent stripping column to remove the extraction solvent from a bottom liquid-phase stream of the pre-separator; a solvent recovery column to remove extraction solvents from the top gas-phase stream of pre-separator and a overhead stream of the solvent stripping column; and a purification column for purifying the overhead stream of the solvent recovery column, in which the extraction solvent is removed with high purity.

Advantageous Effects

As described hereinbefore, the present invention provides a method of separating 1,3-butadiene from a crude C4 stream through acetylene conversion. According to the present invention, in an acetylene conversion process, the concentration of vinylacetylene is decreased to 150 wt ppm or less, after which 1,3-butadiene is recovered using only one extractive distillation column, thereby considerably decreasing the degree of utility and the loss of stream in an extraction process. Further, because the number of units necessary for the process is decreased, the time during which impurities can accumulate in a processing unit is remarkably reduced. Furthermore, the loss of 1,3-butadiene in the acetylene conversion process is minimized to 1 wt % or less, and the recovery of the highly pure 1,3-butadiene separation process is maximized to 98.5 wt % or more, consequently increasing the total recovery of 1,3-butadiene through the entire process.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

BEST MODE

Figure 1:
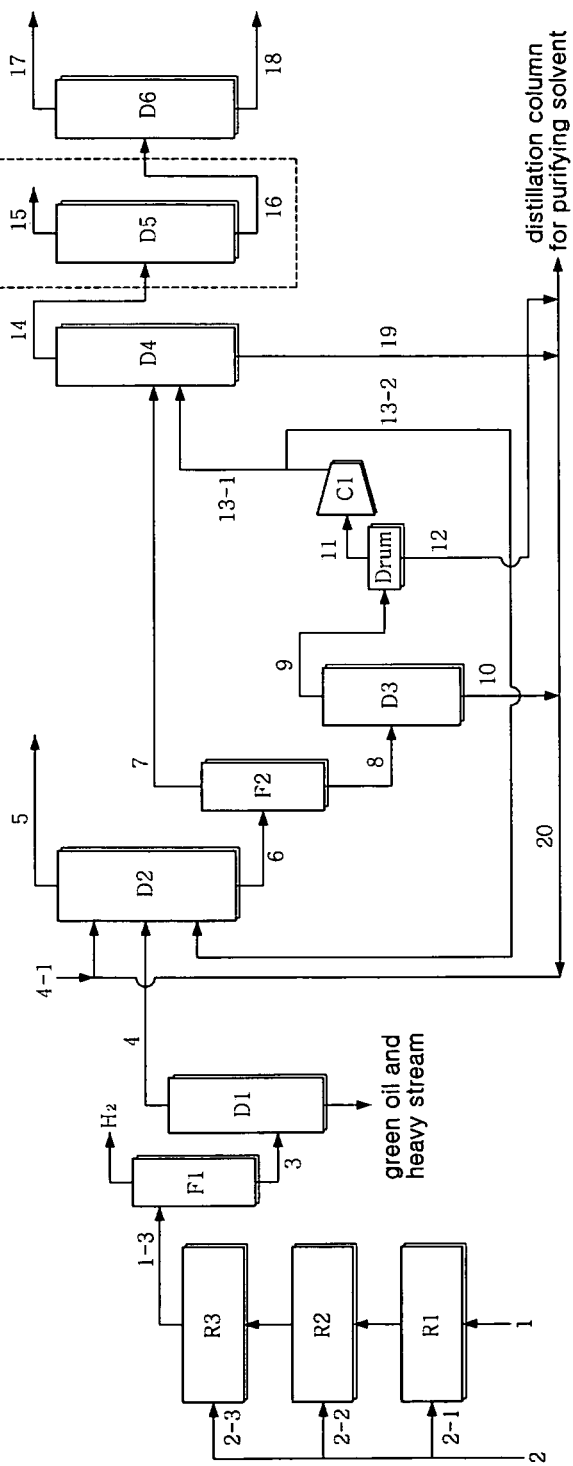
FIG. 1 is a schematic diagram of 1,3-butadiene separation process in accordance to a first embodiment of the present invention.

Hereinafter, a detailed description will be given of the present invention.

The present invention pertains to a method of recovering 1,3-butadiene by introducing a crude C4 stream, produced from a naphtha cracker and containing 0.5~2.5 wt % acetylene, into a reactor filled with an acetylene hydrogenation catalyst to selectively hydrogenate only acetylenes and then supplying the reaction effluent to a subsequent extraction process, and to an equipment used therefor.

The C4 mixtures as the feedstock in this invention are obtained through a naphtha thermal-cracking process and are composed of butane, isobutane, 2-butenes, 1-butene, butadienes, and acetylenes as shown in Table 1. The content of 1,3-butadiene is 30~55 wt % and acetylenes are 0.5~2.5 wt % in the C4 mixtures.

TABLE 1

| Component | wt % | Allowable Range (wt %) |
|---|---|---|
| Cyclopropane | 0.0000 | |
| Propylene | 0.0062 | |
| Isobutane | 0.5269 | |
| Propadiene | 0.0112 | |
| n-Butane | 2.8112 | |
| Methylcyclopropane | 0.0363 | |
| trans-2-Butene | 4.6257 | |
| 1-Butene | 13.5304 | 12~16 |
| Isobutylene | 23.4248 | 22~26 |
| cis-2-Butene | 3.6655 | |
| Cyclobutane | 0.0455 | |
| Isopentane | 0.0741 | |
| 1,2-Butadiene | 0.3169 | |
| Methylacetylene | 0.0000 | ~0.1 |
| 1,3-Butadiene | 49.2362 | 30~55 |
| C5 olefin | 0.0368 | |
| Vinylacetylene | 1.4091 | 0.4~2.1 |
| Ethylacetylene | 0.2431 | 0.1~0.3 |
| Total | 1.0000 | |

According to this invention, the crude C4 mixtures are supplied to a hydrogenation process for selectively hydrogenating the acetylene components. The hydrogenation process requires two or more hydrogenation reactors and proceeds in a top-down flow direction.

The catalyst used for hydrogenation of the C4 mixture containing acetylenes is largely classified into two types; a Cu-based catalyst and a Pd-based catalyst. In this invention, although any catalyst may be used as catalyst for the selective hydrogenation of acetylene in the art, it is desirable to use the Pd-based catalyst which is superior in terms of the stability and hydrogenation activity of the catalyst.

In this invention, liquid-phase hydrogenation in the reactor should be performed under conditions of temperature and pressure to completely dissolve hydrogen in the crude C4 mixtures. If hydrogen is not completely dissolved in the crude C4 mixtures in the hydrogenation reactor, hydrogen bubble in a liquid-vapor mixed stream may be generated. Such hydrogen bubbles cause the rapid hydrogenation of dienes and acetylenes when they come into contact with the catalyst.

The hydrogenation of dienes and acetylenes occur the dramatic temperature increase of part of the catalyst so called a hot spot phenomenon because its reactions are highly exothermic. The olefins in the C4 stream cause polymerization and dimerization (so called "green oil") when the hot spot phenomenon in the catalyst bed occurs. It is difficult to effectively operate hydrogenation process because the polymer and green oil give rise to a pressure drop and clogging of the reactor. Moreover, if the hot spot phenomenon is excessive, the catalytic activity may be decreased by its deformation due to high temperature.

The crude C4 mixtures used in this invention contains about 0.5~2.5 wt % acetylenes such as vinylacetylene, methylacetylene and ethylacetylene. Thus, a reaction pressure over 20 bar is required to completely dissolve hydrogen at 20~60° C., when hydrogen is introduced with 0.7~1.4 molar ratio of hydrogen to acetylene in the C4 stream. In the hydrogenation reaction of the present invention, the reaction pressure is preferably set to 20~40 bar. If the reaction pressure for hydrogenation is lower than 20 bar, hydrogen may not be dissolved completely, and this may generate polymers and green oil. While the pressure is higher than 40 bar, the process cost may be increased, and the acetylene selectivity of the catalyst may be decreased. Theoretically, optimum molar ratio of hydrogen to acetylene is 1:1. However, when the molar ratio of hydrogen to acetylene is very low, the polymerization of C4 olefin and acetylene takes place on the surface site of the catalyst, causing decrease of the activity of the catalyst. While the molar ratio of hydrogen is too high, incomplete dissolution of hydrogen will make it difficult to operate normally.

In the present invention, the selective acetylene converter can include a recycle stream for the stable continuous operation. The recycle procedure is realized in one of three ways described below.

Firstly, when three-hydrogenation reactors are provided, part of the effluent from the $3^{rd}$ reactor is recycled into the $1^{st}$ reactor along with the C4 feed stream. Secondly, part of the effluent from the $1^{st}$ reactor is recycled to the $1^{st}$ reactor together with the feed C4 stream. Lastly, the overhead stream (C4 residue or BBR-1) of an EDC is fed into the $1^{st}$ reactor along with the C4 feed stream. In these ways, the vinylacetylene content in the feed of the reactor is considerably decreased. Moreover, even although the molar ratio of hydrogen to acetylene is 1.2 or higher, hydrogen can easily be dissolved by increasing C4 feed stream as a solvent. In the end, the cycle length of the catalyst will be prolonged with the stability of the catalytic activity.

Additionally, when the butene-butane-raffinate (BBR-1) separated from the EDC overhead are recycled, the fraction of the 1,3-butadiene contained in the feed stream of the reactor is also decreased. Unlike to the case in which the effluent of the hydrogenation reactor is recycled, in this case, the solvent to feed ratio of the 1.sup.st EDC may be greatly reduced. Generally, the extraction solvent is supplied at a mass ratio of about 6.2~6.9 to the feed C4 stream with 40~45 wt % 1,3-butadiene and is supplied at 5.2~5.8 of mass ratio to the feed C4 stream with 30~38 wt % 1,3-butadiene. For example, when about ⅔ of the BBR-1 is recycled to the 1.sup.st reactor, the concentration of 1,3-butadiene of the $1^{st}$ reactor feed stream decreases from 1.2 to 0.9 wt % for vinylacetylene and from 45 to 34 wt % for 1,3-butadiene, leading to an increase of cycle length of the catalyst.

The final conversion of vinylacetylene passed through a plurality of hydrogenation reactors is 98.0~100%, the conversion of ethylacetylene is 60.0~95.5%, and the loss of butadiene is −1.0~1.0 wt %. In order to remove predetermined amounts of C5 or larger heavy stream and green oil, a hydrogen separator may be further mounted downstream of the hydrogenation reactor, whereby unreacted hydrogen is withdrawn and is then supplied into a stripping distillation column.

The gas stream, which contains vinylacetylene having a concentration decreased to 150 wt ppm or less through the plurality of hydrogenation reactors and from which hydrogen and the heavy stream are removed using the hydrogen separator and the stripping distillation column, is supplied to the 1,3-butadiene extraction process along with the extraction solvent.

The 1,3-butadiene extraction process according to the present invention is conducted using one extractive distillation column, a pre-separator, a solvent stripping column, a solvent recovery column, and a purification column. Butadiene, acetylene, and a small amount of cis-2-butene in the stream supplied into the extractive distillation column along with the extraction solvent are introduced into the pre-separator in the state of being dissolved in the solvent. Thereafter, the gas stream, in which the content of the extraction solvent is adjusted through the control of the temperature of the pre-separator, is introduced into the solvent recovery column. In the solvent recovery column using a typical distillation method, the solvent is removed from the gas stream supplied from the pre-separator. The solvent recovery column is operated so that the content of vinylacetylene in the top stream is 30 wt ppm or less, and the top stream of the solvent recovery column is passed through one or two purification columns, thereby obtaining highly pure 1,3-butadiene of 99.6 wt % or more.

Below, the present invention is described in more detail with reference to the accompanying drawings. The processes illustrated in FIGS. 1 to 4 and the following description are set forth to specify the technical spirit disclosed in the claims of the invention, but are not to be construed as the limit of the present invention.

As seen in FIGS. 1 to 4, a crude C4 stream 1, produced from a naphtha cracker, is introduced into a first acetylene hydrogenation reactor R1 along with hydrogen 2-1. The hydrogen is introduced into respective reactors in different amounts. That is, the C4 stream 1-1 passed through the first reactor R1 is introduced into a second reactor R2 along with hydrogen 2-2, and the C4 stream 1-2 passed through the second reactor R2 is introduced into a third reactor R3 along with hydrogen 2-3. The molar ratio of hydrogen to acetylene (based on the feed) is 0.2~1.4, and varies in respective reactors. The amount of hydrogen supplied into respective reactors should not exceed the amount that can be dissolved in the crude C4 stream. Approximately, the molar ratio of hydrogen to acetylene in the first reactor (based on the content of acetylene contained in the feed to be supplied into the first reactor) is preferably adjusted to 1.4~0.7, to 1.0~0.5 in the second reactor, and to 0.2~1.0 in the third reactor.

Figure 2:
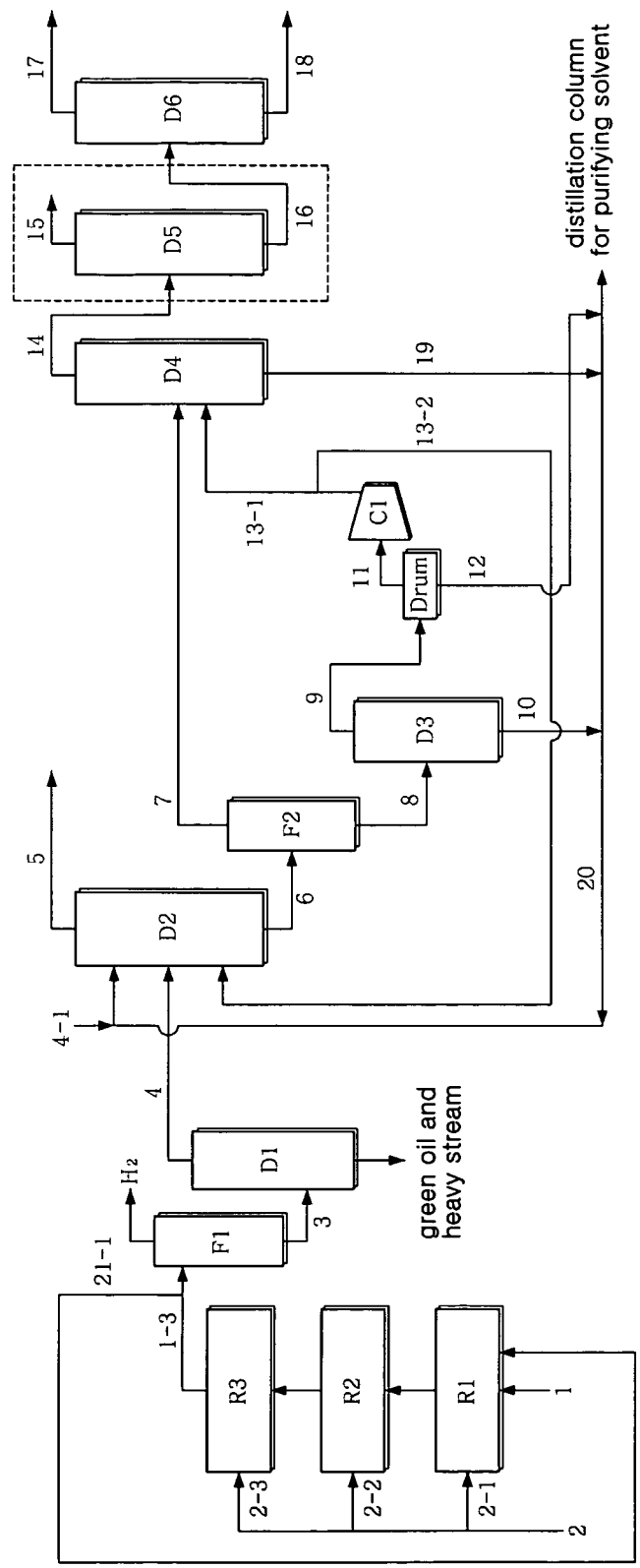
FIG. 2 is a schematic diagram of 1,3-butadiene separation process in accordance to a second embodiment of the present invention.
Figure 3:
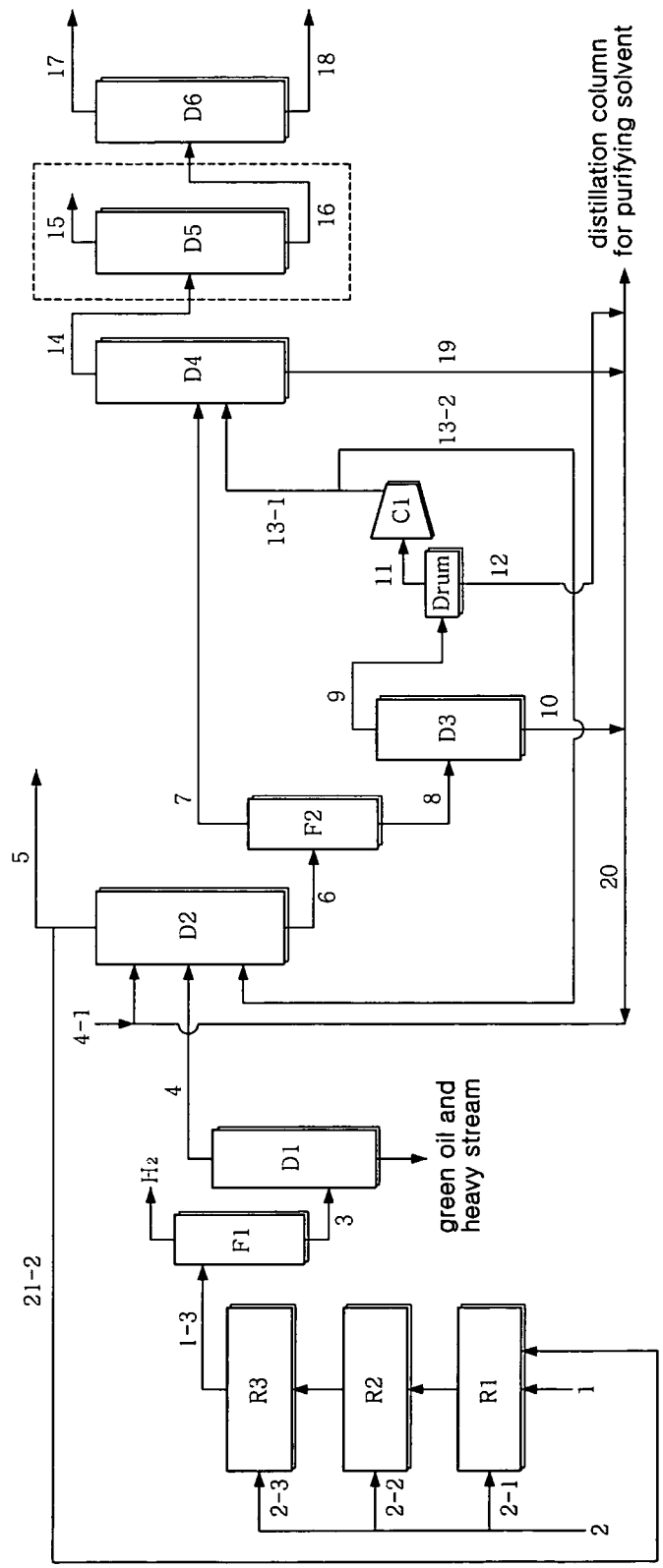
FIG. 3 is a schematic diagram of 1,3-butadiene separation process in accordance to a third embodiment of the present invention.
Figure 4:
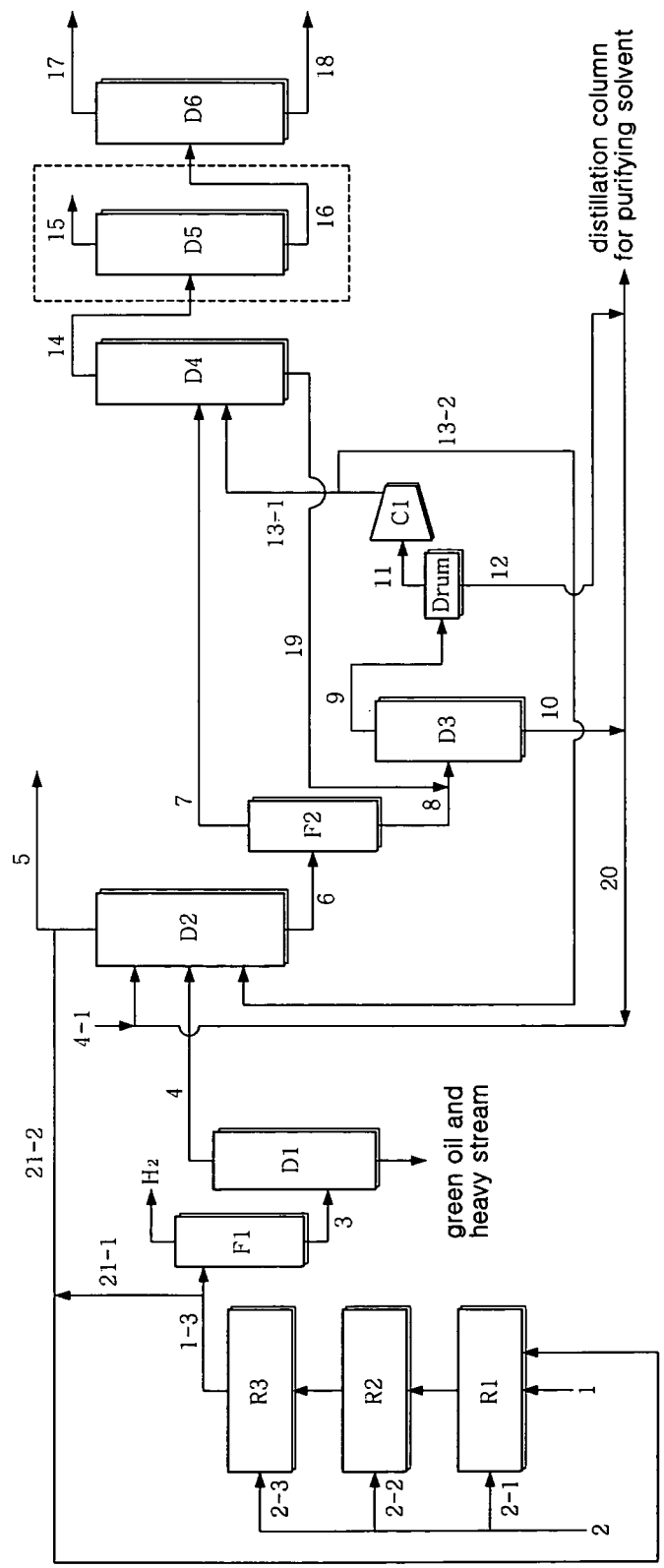
FIG. 4 is a schematic diagram of 1,3-butadiene separation process in accordance to a fourth embodiment of the present invention.

The acetylene conversion process according to the present invention is preferably realized through liquid-phase hydrogenation, using a plurality of hydrogenation reactors, for example, two to four reactors. Preferably, four reactors are provided, three reactors being used for operation, and one reactor waiting for continuous operation upon catalyst regeneration. The operation pressure in the reactor is preferably 20~40 bar, and more preferably 25~35 bar. The operation temperature in the reactor is 20~60° C., and preferably 40~50° C. Because the temperature of the stream passed through the reactor is increased due to reaction heat, a condenser is provided between the reactors so as to decrease the increased temperature to the operation temperature. As seen in FIG. 1, in the case where there is no recirculation to the acetylene hydrogenation reactor, liquid hourly space velocity (LHSV) is 5~20 $hr^{-1}$, and preferably 7~15 $hr^{-1}$. Further, as seen in FIGS. 2 to 4, in the process including a procedure of recirculating the stream of the hydrogenation process or the top stream of the extraction process, the LHSV in the reactor is increased in proportion to the recirculating stream (e.g., when the flow rate ratio of the recirculating stream and the crude C4 feed is 1:1, LHSV is 10~40 h$^{-1}$). The introduction of the stream into the reactor is conducted in a top-down manner (a down flow type).

Stream 1-3 from the acetylene hydrogenation reactor is supplied into a hydrogen separator F1, so that light gas, such as unreacted hydrogen and propylene, is removed from the top of the separator F1. The bottom stream 3 of the separator F1 contains a large amount of C4 stream, and includes green oil and a very small amount of a C5 or larger heavy stream, produced while passing through the reactor. For removal thereof from the bottom stream 3, a stripping distillation column D1 is provided so that the green oil and the heavy stream are removed from the bottom of the distillation column D1. Further, most of the C4 stream 4 is obtained in a gas phase from the top of the stripping distillation column D1, and is then supplied into the middle portion of an extractive distillation column D2. Simultaneously, an extraction solvent is introduced into the upper portion of the extractive distillation column D2. Thereby, butadiene, acetylene, and a small amount of cis-2-butene, having high affinity for the solvent among the components of C4 stream, are obtained from the bottom of the column along with the solvent, whereas raffinate-1 (BBR-1)5, containing butane, isobutane, 2-butene, 1-butene, and isobutene, is withdrawn from the top of the column.

The extraction solvent which is supplied into the extractive distillation column includes a polar solvent, that is, N (nitrogen)-alkylated solvents, examples thereof including dimethylformamide (DMF), diethylformamide, dimethylacetamide, and acetonitrile. These polar solvents in an anhydrous state have good relative volatility and an appropriate boiling point, and are thus suitable for use in the present invention. Among them, particularly useful is dimethylformamide (DMF).

The extractive distillation column D2 is preferably composed of two distillations with each 100 trays and the two distillations are connected in series, resulting in the extractive distillation column including total 200 trays. The bottom temperature of the extractive distillation column D2 is 100~440° C., and preferably 110~130° C.

The bottom stream 6 of the extractive distillation column D2 is introduced into a pre-separator F2. The operation temperature of the pre-separator F2 is 100~140° C. and preferably 120~135° C. The top gas stream of the pre-separator F2 includes the extraction solvent in a content of 7~18 wt %, and preferably 11~13 wt %. When the content of the extraction solvent in the top gas stream of the pre-separator F2 is less than 7 wt %, the case where the content of vinylacetylene in a solvent recovery column D4 is increased cannot be controlled. Conversely, when the content thereof is greater than 18 wt %, the bottom temperature of the pre-separator F2 is too high, and thus, impurities may accumulate. The bottom liquid stream 8 of the pre-separator F2 is introduced into the middle portion of the solvent stripping column D3.

The solvent stripping column D3 functions to withdraw the extraction solvent while maintaining the concentration of vinylacetylene of the bottom stream 10 at 1 wt ppm or less. To this end, the solvent stripping column D3 should be operated at a reflux ratio of at least 2.5 wt % of the extraction solvent which is supplied into the extractive distillation column D2. The top stream 9 of the solvent stripping column D3 includes part of the extraction solvent, and 1,3-butadiene and acetylene are entirely recovered in a state dissolved in the extraction solvent. The stream 9 is supplied into a drum, and vapor stream 11 from the drum is introduced into a compressor C1, and liquid stream 12 from the drum is fed into a solvent purification distillation column (not shown).

Part 13-2 of the stream passed through the compressor C1 is introduced into the lower portion of the extractive distillation column D2, so that the bottom temperature of the extractive distillation column D2 is decreased, thereby inhibiting the polymerization of diene and acetylene. The stream 13-1 and the stream 13-2 are mainly composed of 1,3-butadiene, and small amounts of cis-2-butene, solvent and 1,2-butadiene.

The stream 13-1 is introduced into the middle portion of the solvent recovery column D4 along with the top gas stream 7 of the pre-separator F2. As such, because the stream 7 containing a predetermined amount of the extraction solvent is relatively heavier than the stream 13-1 containing a small amount of solvent, it is supplied at a slightly higher position than the stream 13-1, thereby maximizing the contact between the streams.

The stream 14 containing rich 1,3-butadiene is obtained from the top of the solvent recovery column D4, and the stream 14 contains 98.1 wt % or more of 1,3-butadiene, with less than 1.9 wt % cis-2-butene and 1,2-butadiene, and propadiene. The bottom stream 19 of the solvent recovery column D4 is composed of a large amount of the extraction solvent, with very small amounts of 1,3-butadiene and vinylacetylene. Diene and acetylene are removed from the bottom stream 19 of the solvent recovery column D4, which is then fed again into the extractive distillation column D2 along with the bottom stream 10 of the solvent stripping column D3 and the solvent make-up stream 4-1. Part of the bottom stream 10 of the solvent stripping column D3 is supplied to the solvent purification distillation column, together with the liquid stream 12 of the drum. Stream 20 comprising part of the bottom stream 10 of the solvent stripping column D3 and/or part of the bottom stream 19 of the solvent recovery column D4 is fed into the extractive distillation column D2 along with the solvent make-up stream 4-1.

The main function of the solvent recovery column D4 is to further decrease the content of vinylacetylene contained in 1,3-butadiene as a final product. In the cage where the content of acetylene in the top stream 14 of the solvent recovery column D4 is decreased, the content of 1,3-butadiene, which is mixed to prevent the explosion of vinylacetylene in the bottom stream 19, is increased, and accordingly, the loss of 1,3-butadiene from the top stream 14 is increased, resulting in decreased 1,3-butadiene recovery. Hence, the solvent recovery column is operated in consideration of the specification of final products. The content of acetylene in the top stream 14 is preferably 30 wt ppm or less.

The top stream 14 of the solvent recovery column D4 is supplied into a first purification column D5, and methylacetylene and propadiene are removed from the top stream 15 of the purification column D5. The bottom stream 16 of the first purification column D5 is introduced into a second purification column D6, so that ethylacetylene, cis-2-butene, 1,2-butadiene, and a C5 or larger heavy stream, having low volatility, as the bottom stream 18, are removed, and highly pure 1,3-butadiene is obtained as the top stream 17.

When a crude C4 stream having the same composition is used as a starting material, the top product of the second extractive distillation column in a conventional 1,3-butadiene extraction process using only a 2-column extractive distillation system, and the top stream 14 of the solvent recovery column D4 in a 1,3-butadiene extraction process using one extractive distillation column after a hydrogenation process using a plurality of hydrogenation reactors according to the present invention have the compositions shown in Table 2 below.

TABLE 2

| | Top Stream of 2$^{nd}$ Extractive Distillation Column in Conventional 2-Column Extractive Distillation Process | Top Stream of Solvent Recovery Column in the Inventive Extraction Process |
|---|---|---|
| 1,3-Butadiene | 94.5~96.0 wt % | 98.0 wt % |
| Cis-2-Butene | 3~4 wt % | 1.7 wt % |
| Methylacetylene | 0.02~0.05 wt % | 10 wt ppm |

That is, when compared to the conventional extractive distillation process, the content of 1,3-butadiene was increased from 94.5~96.0 wt % to 98.0 wt %, and the content of cis-2-butene was decreased from 3~4 wt % to 1.7 wt %. Further, the concentration of methylacetylene in the C4 stream was decreased from 0.02~0.05 wt % to 10 wt ppm or less. This is because a considerable amount of methylacetylene is removed along with vinylacetylene in the course of acetylene conversion according to the present invention. Accordingly, of the two purification columns D5, D6 shown in FIGS. 1 to 4, the first purification column D5 may be omitted in the case where the content of propadiene is small or zero.

Generally, because 1,3-butadiene and cis-2-butene have a very small difference in relative volatility therebetween, large numbers of reflux operations and plates are required to distill and separate these materials, entailing the loss of 1,3-butadiene. In the present invention, the content of cis-2-butene is minimized, whereby burdens for separation between two materials in the second purification column D6 may be reduced, and thus, the loss of 1,3-butadiene may be decreased by about 80% compared to the conventional extraction process.

The processes of FIGS. 2 and 3 are almost the same as the process of FIG. 1, with the exception that a system in which part 21-1 of the stream from a final hydrogenation reactor and part 21-2 of the top stream of an extractive distillation column D2 are recirculated respectively to the reactor is provided. For example, in the case where the part 21-1 of the stream from the hydrogenation reactor and/or the part 21-2 of the top stream of the extractive distillation column D2 are recirculated in the same amount as that of the crude C4 feed, the content of vinylacetylene of the total stream, which is introduced into the reactor, is decreased to half of the content of vinylacetylene of the crude C4 feed. The amounts of hydrogen that are introduced are almost the same, and thus, the solubility of hydrogen is increased to thus facilitate the dissolution of hydrogen in the C4 stream. Further, LHSV is doubled, and hence, the linear velocity of the reactor is increased, so that the removal of impurities from the catalyst becomes efficient to some degree. In particular, in the case where the part 21-2 of the top stream 5 of the extractive distillation column D2 is recirculated to the first reactor R1 along with the C4 feed stream 1, the content of 1,3-butadiene of the total stream, which is introduced into the reactor, is decreased, and thereby, the amount of extraction solvent that is used with the feed in the downstream extractive distillation column may be greatly decreased.

In addition, the present invention may further include a procedure for recirculating most of the bottom stream 19 of a solvent recovery column D4 to a solvent stripping column D3, as seen in FIG. 4. The bottom stream 19 of the solvent recovery column, composed of a large amount of extraction solvent and very small amounts of 1,3-butadiene and vinylacetylene, is introduced again into the solvent stripping column D3, thereby decreasing the amount of the stream that is supplied into the solvent purification column and maximally recovering 1,3-butadiene which is lost in the solvent recovery column D4. Most of the bottom stream 19 of the solvent recovery column D4 is introduced into the solvent stripping column D3, and the solvent stripping column D3 is operated at an increased reflux ratio, in order to maximally decrease the content of vinylacetylene of the extraction solvent which is introduced into the extractive distillation column D2.

Consequently, the acetylene conversion process using the plurality of hydrogenation reactors according to the present invention remarkably decreases the content of acetylene before the extraction process, so that the total burden of the 1,3-butadiene extraction process is decreased compared to a conventional 1,3-butadiene extraction process using a 2-column extractive distillation system, thus increasing processing capacity and decreasing the loss of 1,3-butadiene. Further, the number of processing units is decreased, and thus, time during which impurities, which may accumulate in a processing unit, can be produced is considerably reduced.

As mentioned above, when the acetylene conversion process for selectively converting only acetylene in the crude C4 stream produced from the naphtha cracker and containing 30~55 wt % butadiene and 0.5~2.5 wt % acetylene is incorporated with the improved extraction process, the recovery of 1,3-butadiene is increased by 2~3%, and raffinate content is also increased by 2~4%, compared to a conventional extraction process using a 2-column extractive distillation system. As well, due to the simplification of the entire process, the degree of utility is decreased by 10%, and furthermore, as the content of acetylene in the extraction process stream is decreased, the likelihood of the accumulation of impurities attributable to acetylene in a high-temperature heat exchanger may be eliminated, without a stationary section for a long period of time.

MODE FOR INVENTION

Below, the present invention is more specifically described with reference to the following examples.

Example 1

Acetylene Conversion

Using a crude C4 stream having the composition of Table 3 below, a pilot test was conducted. The pilot reactor had a diameter of 6 cm and a length of 120 cm and the amount of catalyst in each reactor was 900 cc, and the flow rate was 9 L/hr, and three reactors were continuously connected without a recirculation procedure. As an acetylene hydrogenation catalyst, a commercial catalyst G-68SK, available from Süd-Chemie Catalysts Japan, Inc., was used. Further, internal condensers were provided between the reactors, so that the temperature of the stream to be introduced into the reactors was constant. As shown in Table 1, the crude C4 stream 1 contained about 44~50 wt % 1,3-butadiene and 1.2~2 wt % acetylene. The temperature of the feed of each reactor was about 40~50° C., and the pressure thereof was 30~31 bar. The LHSV in each reactor was 10 hr$^{-1}$, and hydrogen was sequentially introduced into three reactors at a rate of 34.6, 30.8, and 11.5 NL/hr, corresponding to the molar ratios of hydrogen to acetylene in the crude C4 stream 1 of 0.88, 0.79, and 0.29, respectively. Because hydrogenation is an to exothermic reaction, the reaction temperature was observed to increase in amounts of 15~25° C., 15~20° C., 10~15° C. in respective reactors depending on the amounts of acetylene and hydrogen used. As shown in Table 3 below, the concentration of vinylacetylene in the product after the acetylene conversion was 30~150 wt ppm, the loss of 1,3-butadiene was less than 1 wt %, 1-butene was increased by 8~12 wt %, trans-2-butene was increased by 8~12 wt %, and cis-2-butene was increased by 2~4 wt %.

TABLE 3

| Component, (wt %) | Stream No. | | | |
|---|---|---|---|---|
| | 1 | 1-1 | 1-2 | 1-3 |
| Cyclopropane | 0 | 0 | 0 | 0 |
| Propylene | 0.006203 | 0.005598 | 0.009136 | 0.018268 |
| Isobutane | 0.526879 | 0.533347 | 0.524249 | 0.54862 |
| Propadiene | 0.011248 | 0.009575 | 0.007943 | 0.008871 |
| n-Butane | 2.811236 | 2.817003 | 2.814542 | 2.814623 |
| Methylcyclopropane | 0.036349 | 0.036439 | 0.037125 | 0.036698 |
| trans-2-Butene | 4.625661 | 4.727191 | 5.004148 | 5.074751 |
| 1-Butene | 13.53041 | 13.89438 | 14.4261 | 14.83006 |
| Isobutylene | 23.42484 | 23.44700 | 23.41881 | 23.60476 |
| cis-2-Butene | 3.665463 | 3.723477 | 3.7966 | 3.761678 |
| cyclobutane | 0.045455 | 0.058964 | 0.045773 | 0.044154 |
| Isopentane | 0.074107 | 0.071413 | 0.067017 | 0.065063 |
| 1,2-Butadiene | 0.316942 | 0.302932 | 0.254914 | 0.211092 |
| Methylacetylene | 0 | 0 | 0 | 0 |
| 1,3-Butadiene | 49.23618 | 49.75497 | 49.41457 | 48.90931 |
| C5 olefin | 0.036828 | 0.035849 | 0.036484 | 0.033657 |
| Vinylacetylene | 1.409072 | 0.405708 | 0.058896 | 0.005995 |
| Ethylacetylene | 0.243124 | 0.168280 | 0.069621 | 0.024633 |
| others | — | 0.007874 | 0.014067 | 0.007764 |
| Total | 100.0000 | 100.0000 | 100.0000 | 100.0000 |

1,3-Butadiene Extraction

Process simulation was conducted using a commercially available simulator, Aspen Plus. For accuracy, the simulation was compared to the actual process, and the error range of material resin of the entire process was confirmed to be less than 0.2 wt %. The thermodynamic parameter for the process simulator was ascertained based on the values input to the simulator and the experimental values. The pilot test results were employed as the feed of the available simulator, and, after the plurality of hydrogenation reactors R1, R2, R3, a pre-separator F1, a distillation column D1 for removing green oil and C5 or larger material, and an extraction process were simulated. Unlike a conventional extraction process using a 2-column extractive distillation system, a solvent recovery column D4 was mounted in place of the second extractive distillation column.

In the case where a stream containing 60 wt ppm vinylacetylene resulting from the acetylene conversion process was introduced, 99.6 wt % of 1,3-butadiene, containing 14 wt ppm vinylacetylene, was recovered in an amount of 98.9 wt % or more (in consideration of the loss of reactor, 97.9 wt %). Further, in the case where a stream containing 200 wt ppm vinylacetylene resulting from the acetylene conversion process was introduced to the extraction process, 1,3-butadiene, containing 45 wt ppm vinylacetylene, was recovered to 98.9 wt % or more (in consideration of the loss of reactor, 97.9 wt %), without the manipulation of the process parameter of the extraction process. As such, in order to decrease the concentration of vinylacetylene in the final product to 30 wt ppm or less, the operation conditions of the solvent recovery column D4 were partially changed, and thereby the recovery of 1,3-butadiene was slightly decreased to 98.5 wt %. However, compared to the 1,3-butadiene recovery of 96.5 wt % through a conventional extraction process, according to the acetylene conversion process and the extraction process of the present invention, recovery was increased by 1~1.5 wt %, and the amount of raffinate was increased by 2~8 wt %. Further, at least 10% less energy was consumed, thus exhibiting energy reduction effects. Tables 4 and 5 below show the material resin, temperature, and pressure of respective streams after the reactors and in the 1,3-butadiene extraction process.

TABLE 4

| Stream No. | 1-3 | 3 | 4 | 5 | 6 | 7 | 8 | 9 | 10 |
|---|---|---|---|---|---|---|---|---|---|
| Temperature, C. | 36 | 36.5 | 50.5 | 34.8 | 119.9 | 119.2 | 133 | 113.3 | 166.5 |
| Pressure, bar | 30.4 | 5.9 | 5.9 | 4.5 | 6.3 | 4.1 | 4.2 | 1.3 | 1.5 |
| Mass Flow, kg/hr | 30,008 | 30,008 | 29,936 | 14,923 | 210,669 | 13,218 | 197,451 | 16,106 | 186,631 |
| Composition, wt % | | | | | | | | | |
| Cyclopropane | 0.002 | 0.002 | 0.002 | 0.003 | 0.000 | 0.000 | 0.000 | 0.000 | 0.000 |
| Propylene | 0.018 | 0.018 | 0.018 | 0.037 | 0.000 | 0.000 | 0.000 | 0.000 | 0.000 |
| Isobutane | 0.548 | 0.548 | 0.550 | 1.103 | 0.000 | 0.000 | 0.000 | 0.000 | 0.000 |
| Propadiene | 0.009 | 0.009 | 0.009 | 0.000 | 0.002 | 0.013 | 0.001 | 0.018 | 0.000 |
| n-Butane | 2.814 | 2.814 | 2.820 | 5.657 | 0.000 | 0.000 | 0.000 | 0.000 | 0.000 |
| Methylcyclopropane | 0.034 | 0.034 | 0.029 | 0.000 | 0.006 | 0.048 | 0.003 | 0.044 | 0.000 |
| trans-2-Butene | 5.073 | 5.073 | 5.085 | 10.188 | 0.001 | 0.011 | 0.000 | 0.004 | 0.000 |
| 1-Butene | 14.825 | 14.826 | 14.860 | 29.807 | 0.000 | 0.000 | 0.000 | 0.000 | 0.000 |
| Isobutylene | 23.597 | 23.598 | 23.653 | 47.442 | 0.000 | 0.000 | 0.000 | 0.000 | 0.000 |
| cis-2-Butene | 3.760 | 3.761 | 3.769 | 5.362 | 0.202 | 2.101 | 0.075 | 0.964 | 0.000 |
| Cyclobutane | 0.081 | 0.081 | 0.081 | 0.000 | 0.016 | 0.146 | 0.007 | 0.094 | 0.000 |
| Isopentane | 0.065 | 0.065 | 0.024 | 0.000 | 0.005 | 0.043 | 0.002 | 0.031 | 0.000 |
| 1,2-Butadiene | 0.211 | 0.211 | 0.211 | 0.000 | 0.046 | 0.161 | 0.039 | 0.416 | 0.013 |
| Methylacetylene | 0.000 | 0.000 | 0.000 | 0.000 | 0.000 | 0.000 | 0.000 | 0.000 | 0.000 |
| 1,3-Butadiene | 48.727 | 48.728 | 48.842 | 0.400 | 10.050 | 84.349 | 5.076 | 65.360 | 0.000 |
| C5 olefin | 0.034 | 0.034 | 0.012 | 0.000 | 0.003 | 0.022 | 0.001 | 0.016 | 0.000 |
| Vinylacetylene | 0.006 | 0.006 | 0.006 | 0.000 | 0.002 | 0.006 | 0.001 | 0.019 | 0.000 |
| Ethylacetylene | 0.025 | 0.025 | 0.025 | 0.000 | 0.007 | 0.028 | 0.005 | 0.073 | 0.000 |
| WATER | 0.002 | 0.002 | 0.002 | 0.000 | 0.000 | 0.000 | 0.000 | 0.002 | 0.000 |
| Dimethylformamide | 0.000 | 0.000 | 0.000 | 0.000 | 86.935 | 12.538 | 91.916 | 28.085 | 96.998 |
| Fufural | 0.000 | 0.000 | 0.000 | 0.000 | 1.344 | 0.155 | 1.424 | 0.261 | 1.504 |
| TAR | 0.000 | 0.000 | 0.000 | 0.000 | 1.255 | 0.026 | 1.337 | 0.010 | 1.414 |
| DIMER | 0.167 | 0.167 | 0.002 | 0.000 | 0.126 | 0.352 | 0.111 | 4.604 | 0.070 |
| Hydrogen | 0.002 | 0.000 | 0.000 | 0.000 | 0.000 | 0.000 | 0.000 | 0.000 | 0.000 |

TABLE 5

| Stream No. | 11 | 12 | 13 | 14 | 15 | 16 | 17 | 18 | 19 | 20 |
|---|---|---|---|---|---|---|---|---|---|---|
| Temperature, C. | 36.8 | 36.8 | 77.4 | 21.8 | 40.1 | 47.3 | 32.7 | 51.5 | 76.2 | 35.1 |
| Pressure, bar | 1.0 | 1.0 | 6.9 | 2.5 | 5.1 | 5.3 | 4.3 | 5.1 | 2.6 | 15.7 |
| Mass Flow, kg/hr | 13,328 | 6,748 | 3,510 | 14,770 | 15 | 14,755 | 14,512 | 243 | 1,959 | 188,790 |
| Composition, wt % | | | | | | | | | | |
| Cyclopropane | 0.000 | 0.000 | 0.000 | 0.000 | 0.000 | 0.000 | 0.000 | 0.000 | 0.000 | 0.000 |
| Propylene | 0.000 | 0.000 | 0.000 | 0.000 | 0.000 | 0.000 | 0.000 | 0.000 | 0.000 | 0.000 |
| Isobutane | 0.000 | 0.000 | 0.000 | 0.000 | 0.000 | 0.000 | 0.000 | 0.000 | 0.000 | 0.000 |
| Propadiene | 0.025 | 0.003 | 0.027 | 0.018 | 18.003 | 0.000 | 0.000 | 0.000 | 0.000 | 0.000 |
| n-Butane | 0.000 | 0.000 | 0.000 | 0.000 | 0.000 | 0.000 | 0.000 | 0.000 | 0.000 | 0.000 |
| Methylcyclopropane | 0.063 | 0.011 | 0.062 | 0.000 | 0.000 | 0.000 | 0.000 | 0.004 | 0.438 | 0.000 |
| trans-2-Butene | 0.006 | 0.000 | 0.007 | 0.011 | 0.007 | 0.011 | 0.004 | 0.401 | 0.003 | 0.000 |
| 1-Butene | 0.000 | 0.000 | 0.000 | 0.000 | 0.000 | 0.000 | 0.000 | 0.001 | 0.000 | 0.000 |
| Isobutylene | 0.000 | 0.000 | 0.000 | 0.000 | 0.000 | 0.000 | 0.000 | 0.000 | 0.000 | 0.000 |
| cis-2-Butene | 1.414 | 0.126 | 1.432 | 1.735 | 0.386 | 1.736 | 0.390 | 82.274 | 3.662 | 0.000 |
| Cyclobutane | 0.134 | 0.015 | 0.139 | 0.078 | 0.007 | 0.078 | 0.004 | 4.517 | 0.646 | 0.000 |
| Isopentane | 0.048 | 0.008 | 0.044 | 0.000 | 0.000 | 0.000 | 0.000 | 0.000 | 0.369 | 0.000 |
| 1,2-Butadiene | 0.529 | 0.274 | 0.506 | 0.003 | 0.000 | 0.003 | 0.000 | 0.152 | 1.975 | 0.000 |
| Methylacetylene | 0.000 | 0.000 | 0.000 | 0.000 | 0.000 | 0.000 | 0.000 | 0.000 | 0.000 | 0.000 |
| 1,3-Butadiene | 91.001 | 9.553 | 96.562 | 98.142 | 81.591 | 98.158 | 99.600 | 11.936 | 2.227 | 0.000 |
| C5 olefin | 0.025 | 0.004 | 0.023 | 0.000 | 0.000 | 0.000 | 0.000 | 0.000 | 0.191 | 0.000 |
| Vinylacetylene | 0.023 | 0.012 | 0.023 | 0.004 | 0.000 | 0.004 | 0.001 | 0.162 | 0.051 | 0.000 |
| Ethylacetylene | 0.094 | 0.036 | 0.094 | 0.009 | 0.000 | 0.009 | 0.000 | 0.552 | 0.286 | 0.000 |
| Water | 0.001 | 0.004 | 0.000 | 0.000 | 0.000 | 0.000 | 0.000 | 0.000 | 0.003 | 0.000 |
| Dimethylformamide | 1.213 | 76.860 | 0.280 | 0.000 | 0.000 | 0.000 | 0.000 | 0.000 | 85.115 | 97.000 |
| Fufural | 0.007 | 0.708 | 0.001 | 0.000 | 0.000 | 0.000 | 0.000 | 0.000 | 1.047 | 1.500 |
| Tar | 0.000 | 0.024 | 0.000 | 0.000 | 0.000 | 0.000 | 0.000 | 0.000 | 0.176 | 1.400 |
| Dimer | 5.415 | 12.359 | 0.801 | 0.000 | 0.000 | 0.000 | 0.000 | 0.000 | 3.812 | 0.100 |
| Hydrogen | 0.000 | 0.000 | 0.000 | 0.000 | 0.000 | 0.000 | 0.000 | 0.000 | 0.000 | 0.000 |

Example 2

1,3-butadiene was separated at high purity in the same manner as in Example 1, with the exception that, as seen in FIG. 2, part 21-1 of the stream 1-3 of the third reactor R3 was introduced in the same amount as the crude C4 stream 1 into the first reactor along with the crude C4 stream 1. This is advantageous in that the concentration of vinylacetylene of the stream introduced into the first reactor R1 is decreased to half that of the case without a recirculation procedure, thus increasing the activity stability and selectivity of the catalyst. The LHSV in each reactor was 20 hr$^{-1}$.

The stream containing 42 wt ppm vinylacetylene resulted from the acetylene conversion process, and, through the subsequent extraction process, 99.6 wt % of 1,3-butadiene containing 11 wt ppm vinylacetylene was recovered to 98.9 wt % or more (in consideration of the loss of reactor, 97.9 wt %). Without the manipulation of the process parameter of the extraction process, 1,3-butadiene was recovered to 98.8 wt % or more (in consideration of the loss of reactor, 97.4 wt %).

Table 6 below shows the material resin, temperature, and pressure of respective streams after the reactors and in the 1,3-butadiene extraction process.

TABLE 6

| Stream No. | 1-3 | 21-1 | 3 | 4 | 5 | 6 |
|---|---|---|---|---|---|---|
| Temperature C. | 36.0 | 36.0 | 36.0 | 50.4 | 34.8 | 120.1 |
| Pressure bar | 30.4 | 30.4 | 30.4 | 5.9 | 4.5 | 6.3 |
| Total Flow kg/hr | 60045 | 30000 | 30025 | 29955 | 15904 | 210617 |
| Composition, wt % | | | | | | |
| Cyclopropane | 0.002 | 0.002 | 0.002 | 0.002 | 0.003 | 0.000 |
| Propylene | 0.046 | 0.046 | 0.046 | 0.046 | 0.087 | 0.000 |
| Isobutane | 0.503 | 0.503 | 0.503 | 0.504 | 0.950 | 0.000 |
| Propadiene | 0.010 | 0.010 | 0.010 | 0.010 | 0.000 | 0.003 |
| n-Butane | 2.526 | 2.526 | 2.526 | 2.525 | 4.755 | 0.000 |
| Methylcyclopropane | 0.036 | 0.036 | 0.036 | 0.018 | 0.000 | 0.004 |
| trans-2-Butene | 5.393 | 5.393 | 5.394 | 5.374 | 10.120 | 0.000 |
| 1-Butene | 15.444 | 15.444 | 15.445 | 15.474 | 29.143 | 0.000 |
| Isobutylene | 25.865 | 25.865 | 25.866 | 25.921 | 48.818 | 0.000 |
| cis-2-Butene | 3.860 | 3.860 | 3.861 | 3.801 | 5.725 | 0.147 |
| Cyclobutane | 0.064 | 0.064 | 0.064 | 0.057 | 0.000 | 0.012 |
| 1,2-Butadene | 0.166 | 0.166 | 0.166 | 0.121 | 0.000 | 0.028 |
| Methylacetylene | 0.000 | 0.000 | 0.000 | 0.000 | 0.000 | 0.000 |
| 1,3-Butadiene | 46.011 | 46.011 | 46.016 | 46.109 | 0.400 | 10.107 |
| C5 olefin | 0.038 | 0.038 | 0.038 | 0.013 | 0.000 | 0.003 |
| Vinylacetylene | 0.004 | 0.004 | 0.004 | 0.004 | 0.000 | 0.001 |
| Ethylacetylene | 0.019 | 0.019 | 0.019 | 0.019 | 0.000 | 0.006 |
| Water | 0.002 | 0.002 | 0.002 | 0.001 | 0.000 | 0.000 |
| Dimethylformamide | 0.000 | 0.000 | 0.000 | 0.000 | 0.000 | 86.958 |
| Fufural | 0.000 | 0.000 | 0.000 | 0.000 | 0.000 | 1.345 |
| Tar | 0.000 | 0.000 | 0.000 | 0.000 | 0.000 | 1.255 |

TABLE 6-continued

| | | | | | | |
|---|---|---|---|---|---|---|
| Dimer | 0.000 | 0.000 | 0.000 | 0.000 | 0.000 | 0.131 |
| Hydrogen | 0.010 | 0.010 | 0.000 | 0.000 | 0.000 | 0.000 |

| Stream No. | 7 | 9 | 14 | 17 | 18 | 19 |
|---|---|---|---|---|---|---|
| Temperature C. | 119.2 | 113.2 | 21.8 | 32.7 | 50.4 | 88.7 |
| Pressure bar | 4.1 | 1.3 | 2.5 | 4.3 | 5.1 | 2.6 |
| Total Flow kg/hr | 13149 | 16158 | 13877 | 13698 | 166 | 1880 |
| Composition, wt % | | | | | | |
| Cyclopropane | 0.000 | 0.000 | 0.000 | 0.000 | 0.000 | 0.000 |
| Propylene | 0.000 | 0.000 | 0.000 | 0.000 | 0.000 | 0.000 |
| Isobutane | 0.000 | 0.000 | 0.000 | 0.000 | 0.000 | 0.000 |
| Propadiene | 0.015 | 0.022 | 0.021 | 0.000 | 0.000 | 0.000 |
| n-Butane | 0.000 | 0.000 | 0.000 | 0.000 | 0.000 | 0.000 |
| Methylcyclopropane | 0.033 | 0.030 | 0.000 | 0.000 | 0.004 | 0.292 |
| trans-2-Butene | 0.001 | 0.000 | 0.001 | 0.000 | 0.024 | 0.000 |
| 1-Butene | 0.000 | 0.000 | 0.000 | 0.000 | 0.000 | 0.000 |
| Isobutylene | 0.000 | 0.000 | 0.000 | 0.000 | 0.000 | 0.000 |
| cis-2-Butene | 1.528 | 0.700 | 1.319 | 0.391 | 78.164 | 2.398 |
| Cyclobutane | 0.109 | 0.070 | 0.060 | 0.007 | 4.463 | 0.459 |
| 1,2-Butadene | 0.099 | 0.250 | 0.001 | 0.000 | 0.117 | 1.100 |
| Methylacetylene | 0.000 | 0.000 | 0.000 | 0.000 | 0.000 | 0.000 |
| 1,3-Butadiene | 85.068 | 65.705 | 98.589 | 99.600 | 16.521 | 2.190 |
| C5 olefin | 0.025 | 0.018 | 0.000 | 0.000 | 0.000 | 0.212 |
| Vinylacetylene | 0.005 | 0.014 | 0.003 | 0.001 | 0.138 | 0.036 |
| Ethylacetylene | 0.024 | 0.062 | 0.007 | 0.001 | 0.569 | 0.227 |
| Water | 0.000 | 0.001 | 0.000 | 0.000 | 0.000 | 0.001 |
| Dimethylformamide | 12.545 | 27.928 | 0.000 | 0.000 | 0.000 | 88.116 |
| Fufural | 0.155 | 0.260 | 0.000 | 0.000 | 0.000 | 1.086 |
| Tar | 0.026 | 0.010 | 0.000 | 0.000 | 0.000 | 0.183 |
| Dimer | 0.367 | 4.931 | 0.000 | 0.000 | 0.000 | 3.701 |
| Hydrogen | 0.000 | 0.000 | 0.000 | 0.000 | 0.000 | 0.000 |

Example 3

1,3-butadiene was separated at high purity in the same manner as in Example 1, with the exception that, as seen in FIG. 3, part 21-2 of the top stream of the extractive distillation column D2 was recirculated in a predetermined amount to the first reactor along with the crude C4 stream. The case in which the top stream 21-2 of the extractive distillation column D2 is recirculated is advantageous in that the initial concentration of vinylacetylene introduced into the first reactor R1 and the concentration of 1,3-butadiene are decreased to predetermined levels, thus increasing the activity stability and selectivity of the catalyst. The 46.7 wt % butadiene and 1.3 wt % vinylacetylene in the crude C4 stream 1 were decreased to 35.1 wt % butadiene and 0.99 wt % vinylacetylene, based on the total amount of the stream 1 and the stream 21-2 introduced into the reactor, in the case where 67% of the top stream 5 of the extractive distillation column D2 was used as the recirculating stream 21-2. Further, the LHSV in the reactor was 13.3 hr$^{-1}$. When the amount of C4 stream introduced into the extractive distillation column D2 was increased, the processing capacity was increased but the relative concentration of 1,3-butadiene was decreased. So, although the use of the extraction solvent was decreased, the operation of the extractive distillation column D2 was not greatly changed. The mass ratio of the extraction solvent to the C4 stream introduced into the extractive column D2 was 5.8.

The stream containing 62 wt ppm vinylacetylene resulted from the acetylene conversion process, and, through the subsequent extraction process, 99.6 wt % of 1,3-butadiene containing 22 wt ppm vinylacetylene was recovered to 98.8 wt % or more (in consideration of the loss of reactor, 98.1 wt %).

Table 7 below shows the material resin, temperature, and pressure of respective streams after the reactors and in the 1,3-butadiene extraction process.

TABLE 7

| Stream No. | 21-2 | 1-3 | 3 | 4 | 5 | 6 |
|---|---|---|---|---|---|---|
| Temperature C. | 34.8 | 69.5 | 36.0 | 50.4 | 34.8 | 122.5 |
| Pressure bar | 4.5 | 30.4 | 30.4 | 5.9 | 4.5 | 6.3 |
| Mass Flow kg/hr | 10000 | 40045 | 39998 | 39928 | 15740 | 257270 |
| Composition, wt % | | | | | | |
| Cyclopropane | 0.003 | 0.002 | 0.002 | 0.002 | 0.003 | 0.000 |
| Propylene | 0.079 | 0.051 | 0.051 | 0.051 | 0.079 | 0.000 |
| Isobutane | 0.958 | 0.617 | 0.617 | 0.618 | 0.958 | 0.000 |
| Propadiene | 0.000 | 0.010 | 0.010 | 0.010 | 0.000 | 0.004 |
| n-Butane | 4.798 | 3.093 | 3.094 | 3.093 | 4.798 | 0.000 |
| Methylcyclopropane | 0.000 | 0.027 | 0.027 | 0.014 | 0.000 | 0.004 |
| trans-2-Butene | 10.157 | 6.563 | 6.565 | 6.548 | 10.157 | 0.000 |
| 1-Butene | 28.743 | 18.500 | 18.503 | 18.531 | 28.743 | 0.000 |
| Isobutylene | 49.267 | 31.709 | 31.713 | 31.764 | 49.267 | 0.000 |
| cis-2-Butene | 5.755 | 4.320 | 4.322 | 4.275 | 5.755 | 0.131 |
| Cyclobutane | 0.000 | 0.048 | 0.048 | 0.043 | 0.000 | 0.011 |
| 1,2-Butadene | 0.000 | 0.156 | 0.156 | 0.122 | 0.000 | 0.039 |

TABLE 7-continued

| | | | | | | |
|---|---|---|---|---|---|---|
| Methylacetylene | 0.000 | 0.000 | 0.000 | 0.000 | 0.000 | 0.000 |
| 1,3-Butadiene | 0.240 | 34.822 | 34.829 | 34.885 | 0.240 | 9.718 |
| C5 olefin | 0.000 | 0.029 | 0.029 | 0.010 | 0.000 | 0.003 |
| Vinylacetylene | 0.000 | 0.006 | 0.006 | 0.006 | 0.000 | 0.003 |
| Ethylacetylene | 0.000 | 0.027 | 0.027 | 0.027 | 0.000 | 0.012 |
| Water | 0.000 | 0.001 | 0.002 | 0.001 | 0.000 | 0.000 |
| Dimethylformamide | 0.000 | 0.000 | 0.000 | 0.000 | 0.000 | 87.326 |
| Fufural | 0.000 | 0.000 | 0.000 | 0.000 | 0.000 | 1.350 |
| Tar | 0.000 | 0.000 | 0.000 | 0.000 | 0.000 | 1.260 |
| Dimer | 0.000 | 0.000 | 0.000 | 0.000 | 0.000 | 0.138 |
| Hydrogen | 0.000 | 0.019 | 0.000 | 0.000 | 0.000 | 0.000 |

| Stream No. | 7 | 9 | 14 | 17 | 18 | 19 |
|---|---|---|---|---|---|---|
| Temperature C. | 119.2 | 112.9 | 21.8 | 32.7 | 50.8 | 100.2 |
| Pressure bar | 4.1 | 1.3 | 2.5 | 4.3 | 5.1 | 2.6 |
| Mass Flow kg/hr | 14809 | 20003 | 14008 | 13813 | 181 | 2080 |
| Composition, wt % | | | | | | |
| Cyclopropane | 0.000 | 0.000 | 0.000 | 0.000 | 0.000 | 0.000 |
| Propylene | 0.000 | 0.000 | 0.000 | 0.000 | 0.000 | 0.000 |
| Isobutane | 0.000 | 0.000 | 0.000 | 0.000 | 0.000 | 0.000 |
| Propadiene | 0.024 | 0.033 | 0.030 | 0.000 | 0.000 | 0.000 |
| n-Butane | 0.000 | 0.000 | 0.000 | 0.000 | 0.000 | 0.000 |
| Methylcyclopropane | 0.033 | 0.029 | 0.000 | 0.000 | 0.008 | 0.259 |
| trans-2-Butene | 0.000 | 0.000 | 0.000 | 0.000 | 0.012 | 0.000 |
| 1-Butene | 0.000 | 0.000 | 0.000 | 0.000 | 0.000 | 0.000 |
| Isobutylene | 0.000 | 0.000 | 0.000 | 0.000 | 0.000 | 0.000 |
| cis-2-Butene | 1.439 | 0.656 | 1.387 | 0.389 | 77.817 | 1.502 |
| Cyclobutane | 0.107 | 0.068 | 0.074 | 0.007 | 5.146 | 0.328 |
| 1,2-Butadene | 0.139 | 0.381 | 0.003 | 0.000 | 0.246 | 1.252 |
| Methylacetylene | 0.000 | 0.000 | 0.000 | 0.000 | 0.000 | 0.000 |
| 1,3-Butadiene | 85.060 | 65.237 | 98.483 | 99.600 | 15.267 | 1.996 |
| C5 olefin | 0.024 | 0.017 | 0.000 | 0.000 | 0.000 | 0.185 |
| Vinylacetylene | 0.012 | 0.036 | 0.006 | 0.002 | 0.267 | 0.071 |
| Ethylacetylene | 0.053 | 0.142 | 0.017 | 0.001 | 1.235 | 0.377 |
| Water | 0.000 | 0.001 | 0.000 | 0.000 | 0.000 | 0.001 |
| Dimethylformamide | 12.541 | 27.543 | 0.000 | 0.000 | 0.000 | 89.473 |
| Fufural | 0.155 | 0.257 | 0.000 | 0.000 | 0.000 | 1.104 |
| Tar | 0.026 | 0.010 | 0.000 | 0.000 | 0.000 | 0.186 |
| Dimer | 0.388 | 5.590 | 0.000 | 0.000 | 0.000 | 3.265 |
| Hydrogen | 0.000 | 0.000 | 0.000 | 0.000 | 0.000 | 0.000 |

Example 4

1,3-butadiene was separated at high purity in the same manner as in Example 2, with the exception that, as seen in FIG. 4, most of the bottom stream of the solvent recovery column D4 was introduced into the solvent stripping column D3. This is advantageous in that the amount of the stream which is introduced into the solvent purification column is decreased and in that 1,3-butadiene lost in the solvent recovery column D4 can be maximally recovered. 90 wt % of the bottom stream 19 of the solvent recovery column D4 was introduced into the solvent stripping column D3, and, in order to maintain the content of vinylacetylene of the extraction solvent to be introduced into the extractive distillation column D2 at 1 wt ppm or less, the solvent stripping column D3 was operated with a reflux ratio increased to 3.3 wt % of the extraction solvent from 2.8 wt % thereof. The bottom stream 19 of the solvent recovery column D4 was transferred into the solvent purification column for purifying the extraction solvent, along with the liquid stream 12 after passing the top stream 9 of the solvent stripping column D3 through the drum.

The stream containing 42 wt ppm vinylacetylene resulted from the acetylene conversion process, and, through the subsequent extraction process, 99.6 wt % of 1,3-butadiene containing 24 wt ppm vinylacetylene was recovered to 99.0 wt % or more (in consideration of the loss of the reactor, 98.0 wt %).

Table 8 below shows the material resin, temperature, and pressure of respective streams after the reactors and in the 1,3-butadiene extraction process.

TABLE 8

| Stream No. | '21-1 | '1-3 | 3 | 4 | 5 | 6 |
|---|---|---|---|---|---|---|
| Temperature C. | 36.0 | 61.5 | 36.0 | 50.4 | 34.8 | 119.9 |
| Pressure bar | 30.4 | 30.4 | 30.4 | 5.9 | 4.5 | 6.3 |
| Mass Flow kg/hr | 30000 | 60045 | 30025 | 29955 | 15904 | 210740 |
| Composition, wt % | | | | | | |
| Cyclopropane | 0.002 | 0.002 | 0.002 | 0.002 | 0.003 | 0.000 |
| Propylene | 0.046 | 0.046 | 0.046 | 0.046 | 0.087 | 0.000 |
| Isobutane | 0.503 | 0.503 | 0.503 | 0.504 | 0.950 | 0.000 |
| Propadiene | 0.010 | 0.010 | 0.010 | 0.010 | 0.000 | 0.003 |

TABLE 8-continued

| | | | | | | |
|---|---|---|---|---|---|---|
| n-Butane | 2.526 | 2.526 | 2.526 | 2.525 | 4.755 | 0.000 |
| Methylcyclopropane | 0.036 | 0.036 | 0.036 | 0.018 | 0.000 | 0.032 |
| trans-2-Butene | 5.393 | 5.393 | 5.394 | 5.374 | 10.120 | 0.000 |
| 1-Butene | 15.444 | 15.444 | 15.445 | 15.474 | 29.143 | 0.000 |
| Isobutylene | 25.865 | 25.865 | 25.866 | 25.921 | 48.818 | 0.000 |
| cis-2-Butene | 3.860 | 3.860 | 3.861 | 3.801 | 5.725 | 0.172 |
| Cyclobutane | 0.064 | 0.064 | 0.064 | 0.057 | 0.000 | 0.019 |
| 1,2-Butadene | 0.166 | 0.166 | 0.166 | 0.121 | 0.000 | 0.040 |
| Methylacetylene | 0.000 | 0.000 | 0.000 | 0.000 | 0.000 | 0.000 |
| 1,3-Butadiene | 46.011 | 46.011 | 46.016 | 46.109 | 0.400 | 10.060 |
| C5 olefin | 0.038 | 0.038 | 0.038 | 0.013 | 0.000 | 0.022 |
| Vinylacetylene | 0.004 | 0.004 | 0.004 | 0.004 | 0.000 | 0.002 |
| Ethylacetylene | 0.019 | 0.019 | 0.019 | 0.019 | 0.000 | 0.016 |
| Water | 0.002 | 0.002 | 0.002 | 0.001 | 0.000 | 0.000 |
| Dimethylformamide | 0.000 | 0.000 | 0.000 | 0.000 | 0.000 | 86.907 |
| Fufural | 0.000 | 0.000 | 0.000 | 0.000 | 0.000 | 1.344 |
| Tar | 0.000 | 0.000 | 0.000 | 0.000 | 0.000 | 1.254 |
| Dimer | 0.000 | 0.000 | 0.000 | 0.000 | 0.000 | 0.130 |
| Hydrogen | 0.010 | 0.010 | 0.000 | 0.000 | 0.000 | 0.000 |

| Stream No. | 7 | 9 | 14 | 17 | 18 | 19 |
|---|---|---|---|---|---|---|
| Temperature C. | 119.2 | 112.3 | 21.8 | 32.7 | 51.4 | 132.0 |
| Pressure bar | 4.1 | 1.3 | 2.5 | 4.3 | 5.1 | 2.6 |
| Mass Flow kg/hr | 13270 | 16613 | 13964 | 13735 | 215 | 1824 |
| Composition, wt % | | | | | | |
| Cyclopropane | 0.000 | 0.000 | 0.000 | 0.000 | 0.000 | 0.000 |
| Propylene | 0.000 | 0.000 | 0.000 | 0.000 | 0.000 | 0.000 |
| Isobutane | 0.000 | 0.000 | 0.000 | 0.000 | 0.000 | 0.000 |
| Propadiene | 0.015 | 0.021 | 0.021 | 0.000 | 0.000 | 0.000 |
| n-Butane | 0.000 | 0.000 | 0.000 | 0.000 | 0.000 | 0.000 |
| Methylcyclopropane | 0.250 | 0.544 | 0.000 | 0.000 | 0.029 | 2.674 |
| trans-2-Butene | 0.001 | 0.000 | 0.001 | 0.000 | 0.022 | 0.000 |
| 1-Butene | 0.000 | 0.000 | 0.000 | 0.000 | 0.000 | 0.000 |
| Isobutylene | 0.000 | 0.000 | 0.000 | 0.000 | 0.000 | 0.000 |
| cis-2-Butene | 1.782 | 1.146 | 1.590 | 0.389 | 78.501 | 2.999 |
| Cyclobutane | 0.177 | 0.206 | 0.110 | 0.007 | 6.675 | 0.810 |
| 1,2-Butadene | 0.138 | 0.503 | 0.002 | 0.000 | 0.151 | 1.691 |
| Methylacetylene | 0.000 | 0.000 | 0.000 | 0.000 | 0.000 | 0.000 |
| 1,3-Butadiene | 84.291 | 63.890 | 98.245 | 99.600 | 12.773 | 2.037 |
| C5 olefin | 0.192 | 0.376 | 0.000 | 0.000 | 0.000 | 1.963 |
| Vinylacetylene | 0.009 | 0.040 | 0.006 | 0.002 | 0.269 | 0.078 |
| Ethylacetylene | 0.066 | 0.267 | 0.025 | 0.001 | 1.578 | 0.715 |
| Water | 0.000 | 0.001 | 0.000 | 0.000 | 0.000 | 0.001 |
| Dimethylformamide | 12.537 | 27.016 | 0.000 | 0.000 | 0.000 | 82.447 |
| Fufural | 0.155 | 0.250 | 0.000 | 0.000 | 0.000 | 1.015 |
| Tar | 0.026 | 0.009 | 0.000 | 0.000 | 0.000 | 0.171 |
| Dimer | 0.362 | 5.732 | 0.000 | 0.000 | 0.000 | 3.398 |
| Hydrogen | 0.000 | 0.000 | 0.000 | 0.000 | 0.000 | 0.000 |

Example 5

Figure 5:
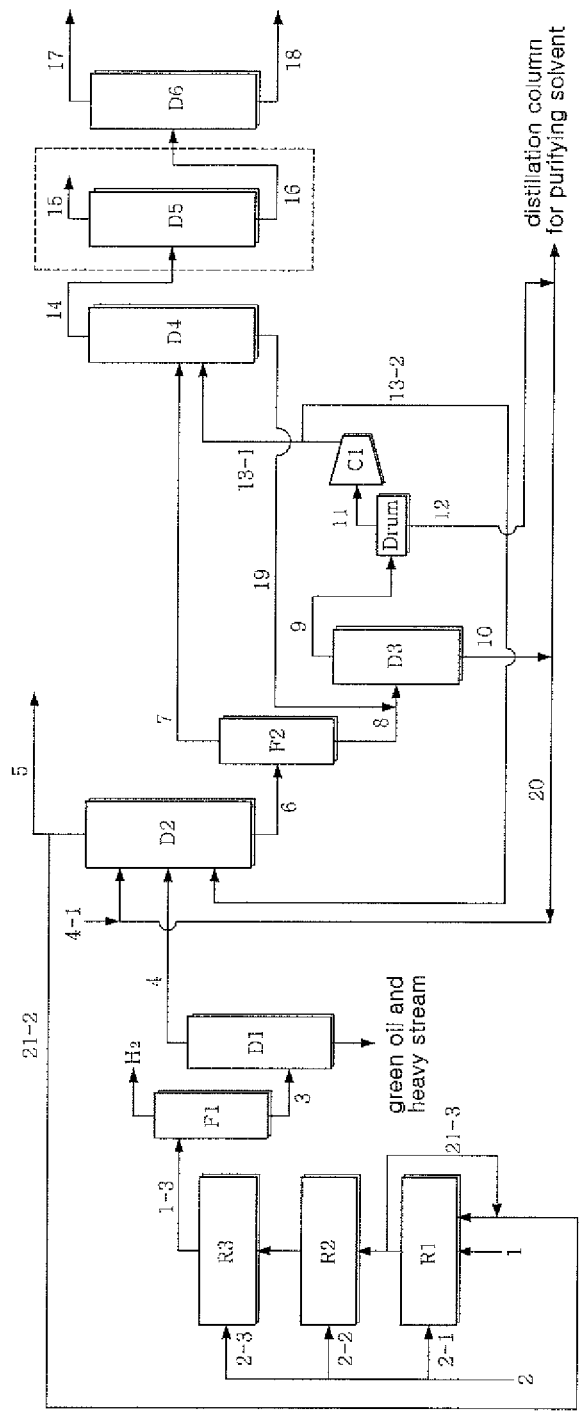
FIG. 5 is a schematic diagram of 1,3-butadiene separation process in accordance to a fifth embodiment of the present invention.

1,3-butadiene was separated at high purity in the same manner as in Example 4, with the exception that, as seen in FIG. 5, the stream 21-3 passed through the first reactor is recirculated to the first reactor. This is advantageous in that the amount of the stream which is introduced into the solvent purification column is decreased, also, 1,3-butadiene lost in the solvent recovery column D4 can be maximally recovered, and the ratio of hydrogen and acetylene is easily adjustable. The method of recycling the stream passed through the last reactor to the first reactor has an advantage in that contact time is increased, and linear speed of inside reactor is increased, while it has a shortcoming in that some of oligomer is generated as hydrogenation is proceeding, and thus generated oligomer which is generally called to "Green oil" is continuously maintained.

90 wt % of the bottom stream 19 of the solvent recovery column D4 was introduced into the solvent stripping column D3, and, in order to maintain the content of vinylacetylene of the extraction solvent to be introduced into the extractive distillation column D2 at 1 wt ppm or less, the solvent stripping column D3 was operated with a reflux ratio increased to 3.3 wt % of the extraction solvent from 2.8 wt % thereof. The bottom stream 19 of the solvent recovery column D4 was transferred into the solvent purification column for purifying the extraction solvent, along with the liquid stream 12 after passing the top stream 9 of the solvent stripping column D3 through the drum.

The stream containing 42 wt ppm vinylacetylene resulted from the acetylene conversion process, and, through the subsequent extraction process, 99.6 wt % of 1,3-butadiene containing 23 wt ppm vinylacetylene was recovered to 98.9 wt % or more (in consideration of the loss of the reactor, 97.8 wt %). Also, an amount of usage of hydrogen is more 11% lessened than the method as disclosed in FIG. 2.

Table 9 below shows the material resin, temperature, and pressure of respective streams after the reactors and in the 1,3-butadiene extraction process.

TABLE 9

| Stream No. | 1 | 21-1 | 1-3 | 3 | 4 | 5 | 6 |
|---|---|---|---|---|---|---|---|
| Temperature C. | 27 | 36 | 44.8 | 36 | 50.4 | 34.8 | 119.9 |
| Pressure bar | 10.82 | 30.433 | 30.433 | 30.433 | 5.917 | 4.544 | 6.299 |
| Mass Flow kg/hr | 30000 | 60035 | 30045 | 30018 | 29948 | 15837 | 209547 |
| Composition, wt % | | | | | | | |
| Cyclopropane | 0.0017 | 0.0017 | 0.0017 | 0.0017 | 0.0017 | 0.0031 | 0.0000 |
| Propylene | 0.0031 | 0.0381 | 0.0453 | 0.0452 | 0.0453 | 0.0857 | 0.0000 |
| Isobutane | 0.5039 | 0.5033 | 0.5032 | 0.5031 | 0.5043 | 0.9534 | 0.0000 |
| Propadiene | 0.0249 | 0.0130 | 0.0105 | 0.0105 | 0.0105 | 0.0000 | 0.0027 |
| n-Butane | 2.5293 | 2.5264 | 2.5256 | 2.5261 | 2.5248 | 4.7738 | 0.0000 |
| Methylcyclopropane | 0.0359 | 0.0359 | 0.0359 | 0.0359 | 0.0184 | 0.0000 | 0.0307 |
| trans-2-Butene | 4.8966 | 5.3036 | 5.3768 | 5.3782 | 5.3582 | 10.1304 | 0.0001 |
| 1-Butene | 13.7704 | 15.0761 | 15.3614 | 15.3635 | 15.3926 | 29.1039 | 0.0000 |
| Isobutylene | 25.9034 | 25.8732 | 25.8646 | 25.8669 | 25.9222 | 49.0127 | 0.0000 |
| cis-2-Butene | 3.6553 | 3.8219 | 3.8479 | 3.8491 | 3.7907 | 5.5368 | 0.1946 |
| Cyclobutane | 0.0642 | 0.0641 | 0.0641 | 0.0641 | 0.0568 | 0.0001 | 0.0193 |
| 1,2-Butadene | 0.2767 | 0.1936 | 0.1780 | 0.1781 | 0.1298 | 0.0000 | 0.0418 |
| Methylacetylene | 0.0259 | 0.0044 | 0.0000 | 0.0000 | 0.0000 | 0.0000 | 0.0000 |
| 1,3-Butadiene | 46.7094 | 46.2114 | 46.1036 | 46.1105 | 46.2038 | 0.4000 | 10.0117 |
| C5 olefin | 0.0384 | 0.0384 | 0.0384 | 0.0384 | 0.0133 | 0.0000 | 0.0211 |
| Vinylacetylene | 1.3173 | 0.2288 | 0.0042 | 0.0042 | 0.0042 | 0.0000 | 0.0023 |
| Ethylacetylene | 0.2416 | 0.0598 | 0.0224 | 0.0224 | 0.0222 | 0.0000 | 0.0172 |
| Water | 0.0020 | 0.0020 | 0.0020 | 0.0020 | 0.0012 | 0.0000 | 0.0002 |
| Dimethylformaide | 0.0000 | 0.0000 | 0.0000 | 0.0000 | 0.0000 | 0.0000 | 86.9307 |
| Fufural | 0.0000 | 0.0000 | 0.0000 | 0.0000 | 0.0000 | 0.0000 | 1.3442 |
| Tar | 0.0000 | 0.0000 | 0.0000 | 0.0000 | 0.0000 | 0.0000 | 1.2545 |
| Dimer | 0.0000 | 0.0000 | 0.0000 | 0.0000 | 0.0000 | 0.0000 | 0.1289 |
| Hydrogen | 0.0000 | 0.0043 | 0.0145 | 0.0000 | 0.0000 | 0.0000 | 0.0000 |

| Stream No. | 7 | 9 | 14 | 17 | 18 | 19 |
|---|---|---|---|---|---|---|
| Temperature C. | 119.2 | 112.4 | 21.8 | 32.7 | 51.8 | 132 |
| Pressure bar | 4.053 | 1.337 | 2.543 | 4.328 | 5.054 | 2.641 |
| Mass Flow kg/hr | 13139 | 16534 | 14020 | 13761 | 244 | 203 |
| Composition, wt % | | | | | | |
| Cyclopropane | 0.0000 | 0.0000 | 0.0000 | 0.0000 | 0.0000 | 0.0000 |
| Propylene | 0.0000 | 0.0000 | 0.0000 | 0.0000 | 0.0000 | 0.0000 |
| Isobutane | 0.0000 | 0.0000 | 0.0000 | 0.0000 | 0.0000 | 0.0000 |
| Propadiene | 0.0166 | 0.0230 | 0.0225 | 0.0000 | 0.0000 | 0.0000 |
| n-Butane | 0.0000 | 0.0000 | 0.0000 | 0.0000 | 0.0000 | 0.0000 |
| Methylcyclopropane | 0.2431 | 0.5393 | 0.0004 | 0.0000 | 0.0258 | 2.6752 |
| trans-2-Butene | 0.0010 | 0.0004 | 0.0010 | 0.0004 | 0.0344 | 0.0005 |
| 1-Butene | 0.0000 | 0.0000 | 0.0000 | 0.0000 | 0.0000 | 0.0000 |
| Isobutylene | 0.0000 | 0.0000 | 0.0000 | 0.0000 | 0.0000 | 0.0000 |
| cis-2-Butene | 2.0214 | 1.3146 | 1.7912 | 0.3914 | 80.7031 | 3.5139 |
| Cyclobutane | 0.1762 | 0.2074 | 0.1093 | 0.0052 | 5.9772 | 0.8240 |
| 1,2-Butadene | 0.1452 | 0.5336 | 0.0025 | 0.0000 | 0.1453 | 1.8374 |
| Methylacetylene | 0.0000 | 0.0000 | 0.0000 | 0.0000 | 0.0000 | 0.0000 |
| 1,3-Butadiene | 84.0510 | 63.6777 | 98.0374 | 99.6000 | 11.2407 | 2.0407 |
| C5 olefin | 0.1867 | 0.3734 | 0.0000 | 0.0000 | 0.0000 | 1.9627 |
| Vinylacetylene | 0.0089 | 0.0387 | 0.0065 | 0.0023 | 0.2480 | 0.0784 |
| Ethylacetylene | 0.0727 | 0.2997 | 0.0291 | 0.0007 | 1.6259 | 0.8220 |
| Water | 0.0002 | 0.0010 | 0.0000 | 0.0000 | 0.0000 | 0.0015 |
| Dimethylformaide | 12.5371 | 27.0428 | 0.0000 | 0.0000 | 0.0000 | 81.6508 |
| Fufural | 0.1548 | 0.2499 | 0.0000 | 0.0000 | 0.0000 | 1.0050 |
| Tar | 0.0260 | 0.0089 | 0.0000 | 0.0000 | 0.0000 | 0.1687 |
| Dimer | 0.3592 | 5.6897 | 0.0000 | 0.0000 | 0.0000 | 3.4197 |
| Hydrogen | 0.0000 | 0.0000 | 0.0000 | 0.0000 | 0.0000 | 0.0000 |

The invention claimed is:

1. A method of separating 1,3-butadiene from a crude C4 stream, comprising:
   (a) supplying the crude C4 stream comprising 30 to 55 wt % 1,3-butadiene and 0.5 to 2.5 wt % acetylenes into a plurality of hydrogenation reactors comprising a first hydrogenation reactor, a second hydrogenation reactor and a third hydrogenation reactor arranged in series;
   (b) selectively hydrogenating acetylenes in the crude C4 stream under liquid-phase hydrogenation conditions at a temperature of 20 to 60° C. and a pressure of 20 to 40 bar to produce a hydrogenated C4 stream with a content of vinylacetylene of 70 wt ppm or less, in which hydrogen is supplied to each of the hydrogenation reactors in such an amount that a molar ratio of hydrogen to acetylene in the first hydrogenation reactor, the second hydrogenation reactor and the third hydrogenation reactor is in a range of 1.4 to 0.7, 1.0 to 0.5 and 0.2 to 1.0, respectively, based on the content of acetylenes in the C4 stream supplied to the first reactor;
   (b-1) introducing the hydrogenated C4 stream from the plurality of hydrogenation reactors into a hydrogen separator to remove unreacted hydrogen and light gas, and then removing green oil and C5 or larger hydrocarbons using a stripping distillation column;

(c) supplying a C4 stream from the top of the stripping distillation column into an extractive distillation column along with an extraction solvent to conduct extractive distillation;

(d) introducing a bottom stream of the extractive distillation column into a pre-separator, and then supplying a top gas stream of the pre-separator into a solvent recovery column and supplying a bottom liquid stream of the pre-separator into a solvent stripping column;

(e) supplying a top stream of the solvent stripping column, containing part of the extraction solvent, butadiene, and acetylenes, into the solvent recovery column along with the top stream of the pre-separator; and (f) introducing a top stream of the solvent recovery column, from which the extraction solvent is removed, into a purification column to obtain 1,3-butadiene, wherein (i) a part of the top stream of the extractive distillation column is recirculated to the first hydrogenation reactor, (ii) both a part of the hydrogenated C4 stream passed through the plurality of hydrogenation reactors and a part of the top stream of the extractive distillation column are recirculated to the first hydrogenation reactor, or (iii) both a part of a stream passed through the first hydrogenation reactor and a part of the top stream of the extractive distillation column are recirculated to the first hydrogenation reactor, in which the stream or streams recirculated in (i), (ii) or (iii) comprises C4 hydrocarbons, and are fed into the first hydrogenation reactor along with in the crude C4 stream to decrease the concentration of acetylenes in the crude C4 stream, and wherein the method is carried out using only a single extractive distillation column.

2. The method as set forth in claim 1, wherein the liquid-phase hydrogenation is conducted in a down flow manner.

3. The method as set forth in claim 1, wherein the extraction solvent is one or more selected from a group consisting of dimethylformamide (DMF), diethylformamide, dimethylacetamide, and acetonitrile.

4. The method as set forth in claim 1, wherein a content of the extraction solvent contained in the top gas stream of the pre-separator is 7-18 wt %.

5. The method as set forth in claim 1, wherein the top gas stream of the pre-separator and the top stream of the solvent stripping column are introduced into a middle portion of the solvent recovery column, and the top gas stream of the pre-separator is introduced at a higher position than the top stream of the solvent stripping column.

6. The method as set forth in claim 1, further comprising passing the top stream of the solvent stripping column through a drum to separate a vapor stream, and supplying the separated vapor stream into a compressor to thus compress it, before introducing the top stream of the solvent stripping column into the solvent recovery column.

7. The method as set forth in claim 1, wherein a bottom stream of the solvent stripping column and a the bottom stream of the solvent recovery column are introduced again into the extractive distillation column.

8. The method as set forth in claim 1, wherein a bottom stream of the solvent stripping column and a bottom stream of the solvent recovery column are introduced again into the extractive distillation column.

9. The method as set forth in claim 1, wherein the part of the hydrogenated C4 stream passed through the plurality of hydrogenation reactors is recovered from a point after the final hydrogenation reactor among the plurality of hydrogenation reactors, and then recirculated to the first hydrogenation reactor.

10. The method as set forth in claim 1, wherein a bottom stream of the solvent recovery column is introduced into the solvent stripping column.

11. The method as set forth in claim 1, wherein the liquid phase hydrogenation is carried out under a pressure of 25 to 40 bar.

12. The method as set forth in claim 11, wherein the liquid phase hydrogenation is carried out under a pressure of 30 to 40 bar.

13. The method as set forth in claim 1, wherein the crude C4 stream further comprises 12 to 16 wt % of 1-butene and 22 to 26 wt % of isobutylene.

* * * * *